United States Patent [19]

Drauz et al.

[11] 4,376,864
[45] Mar. 15, 1983

[54] CYCLIC ACETALS OF GLUTAMIC ACID-γ-SEMIALDEHYDE, PROCESS FOR THEIR PRODUCTION AND USE

[75] Inventors: Karlheinz Drauz, Freigericht; Axel Kleemann; Marc Samson, both of Hanau, all of Fed. Rep. of Germany

[73] Assignee: Degussa AG, Frankfurt, Fed. Rep. of Germany

[21] Appl. No.: 320,131

[22] Filed: Nov. 10, 1981

[30] Foreign Application Priority Data

Nov. 15, 1980 [DE] Fed. Rep. of Germany ....... 3043159

[51] Int. Cl.³ .................. C07D 317/30; C07D 319/06
[52] U.S. Cl. ..................................... 549/373; 549/451
[58] Field of Search ............................... 549/373, 451

[56] References Cited

U.S. PATENT DOCUMENTS 2,500,155 3/1950 Croxall et al. ................. 549/372 X Primary Examiner—Richard Raymond
Attorney, Agent, or Firm—Cushman, Darby & Cushman

[57] ABSTRACT

The invention is directed to cyclic acetals of glutamic acid-γ-semialdehyde of the formula

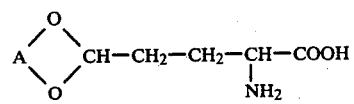
(I)

in which A is an unsubstituted alkylene group having 2 to 3 carbon atoms or such an alkylene group substituted by 1 to 2 methyl groups and to a method of producing a compound of formula (I) by reaction of a compound of the general formula

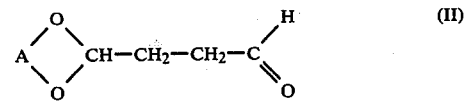
(II)

in which A is as defined above with hydrogen cyanide or a cyanide ion supplying compound, ammonia or an ammonium ion supplying compound and carbon dioxide or a carbonate ion supplying compound and basic hydrolysis of the reaction mixture obtained and to using the compound of formula (I) to produce D,L-proline.

1 Claim, No Drawings

CYCLIC ACETALS OF GLUTAMIC ACID-γ-SEMIALDEHYDE, PROCESS FOR THEIR PRODUCTION AND USE

SUMMARY OF THE INVENTION

The present invention is directed to cyclic acetals of glutamic acid-γ-semialdehyde of the formula

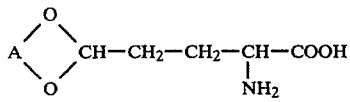
(I)

in which A is an unsubstituted alkylene group with 2 or 3 carbon atoms or such an alkylene group substituted by 1 to 2 methyl groups and a process for its production.

These cyclic acetals of glutamic acid-γ-semialdehyde are valuable intermediate products for the production of D,L-proline. A further object of the invention therefore is the use of the products to produce D,L-proline.

The cyclic acetals of glutamic acid-γ-semialdehyde of general formula (I) can be produced by a process comprising (a) reacting a compound of the general formula

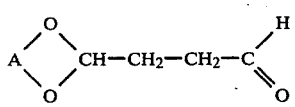
(II)

in which A is as defined above in aqueous or aqueous-alcoholic solution with hydrogen cyanide or a cyanide ion supplying compound, ammonia or an ammonium ion supplying compound and carbon dioxide or a carbonate ion supplying compound and (b) hydrolyzing the reaction mixture obtained in step (a) under basic conditions.

The two reaction steps of the process of the invention proceed with high conversion.

Since the compounds employed of general formula (II) are also obtainable through hydroformylation of the corresponding 2-vinyl-1,3-dioxolane or 2-vinyl-1,3-dioxane and the latter are easily obtainable in high yields by acetalization of acrolein with the corresponding 1,2 glycol or 1,3-glycol, the cyclic acetals of glutamic acid-γ-semialdehyde of the general formula (I) can be produced economically. Since the compounds of general formula (I) then likewise can be changed into D,L-proline easily and with high yields there is in all opened up a new advantageous, economical manner starting from acrolein to form D,L-proline.

Examples of compounds employed of general formula (II) are 2-(2'-formylethyl)-1,3-dioxolane, 2-(2'-formylethyl)-4-methyl-1,3-dioxolane, 2-(2'-formylethyl)-4,5-dimethyl-1,3-dioxolane, 2-(2'-formylethyl)-1,3-dioxane, 2-(2'-formylethyl)-4-methyl-1,3-dioxane or 2-(2'formylethyl)-5,5-dimethyl-1,3-dioxane.

The compounds of general formula (II) are reacted in a first reaction step which is known in itself for the formation of hydantoins from aldehydes with hydrogen cyanide or a cyanide ion supplying compound, such as sodium cyanide or potassium cyanide, with ammonia or an ammonium ion supplying compound, such as ammonium hydroxide or ammonium chloride, and with carbon dioxide or a carbonate ion supplying compound, such as sodium or potassium bicarbonate, sodium or potassium carbonate, or sodium or potassium carbamate. There can also be employed compounds which simultaneously supply cyanide and ammonium ions, such as ammonium cyanide or which simultaneously supply ammonium and carbonate ions, such as ammonium-carbonate or ammonium carbamate.

The reaction in the first reaction step takes place in water or in a mixture of water and methanol or ethanol. It can be undertaken in a wide temperature range. Preferably there is employed a temperature between 30+ and 90° C., because in this range a satisfactory reaction speed is attained and the perhaps necessary superatmospheric pressure does not create an industrial obstacle.

The amounts of the individual reactants can be varied within a wide range. Preferably per mole of compound of general formula (II) there is employed 1 to 1.5 moles of hydrogen cyanide or cyanide ion supplying compound, 2 to 15 moles of ammonia or an ammonium ion supplying compound and 1 to 2 moles of carbon dioxide or a carbonate ion supplying compound. The compounds of general formula (II) can be reacted simultaneously with all three other reactants. However, it is likewise also possible to first react it with the cyanide component and subsequently react simultaneously with the two other components, or first to react only with the cyanide component, then react only with the ammonium component and only after that react with the carbon dioxide or carbonate component. It is especially advantageous to have the compound of general formula (II) dissolved in methanol or ethanol and to slowly feed this solution into an aqueous solution or suspension of the other reactants at the desired reaction temperature. To achieve high conversions there is recommended a suitable post reaction time of for example 5 hours after the time of the feeding in.

Depending on the reaction conditions used the reaction mixture after carrying out the first reaction step contains besides the expected hydantoin of the general formula

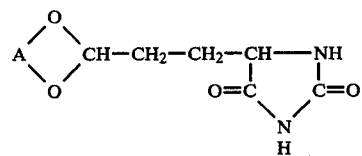
(III)

also a more or less large portion of the α-N-carbamoyl-carboxylic acid amide of the general formula

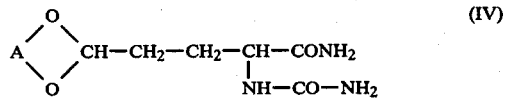
(IV)

wherein in formula (III) and (IV) A is again as defined above.

However, it is not necessary to separate the two reaction products, since both of them are transformed in subsequent reaction step (b) to the cyclic acetals of glutamic acid-γ-semialdehyde. However, it can be suitable before carrying out the second reaction step (b) to remove the ammonium salts contained in the crude reaction mixture of the first reaction step (a), to distill off the optionally present alcohol and to concentrate the reaction mixture under reduced pressure.

Them the mixture of compounds of general formula (III) and (IV) obtained in step (a) is reacted under basic hydrolysis conditions for forming the α-aminoacids from the corresponding substituted hydantoins in a manner known of itself. Preferably there are used alkali or alkaline earth metal hydroxides or alkaline metal carbonates in aqueous medium. For example there can be used with good success NaOH, KOH, $Na_2CO_3$, $K_2CO_3$, $Ca(OH)_2$ or $Ba(OH)_2$. The reaction temperature can be varied in a wide range between 20° C. and 200° C. Preferred are temperatures between 120° C. and 170° C. since in this range satisfactory reaction speeds can be attained. Especially preferred saponification conditions are temperatures between 130° and 160° C., reaction times of 0.5 to 3 hours and a mole ratio of substrate to base of 1:2 to 1:2.5.

After the hydrolysis the reaction mixture is neutralized and the glutamic acid-γ-semialdehyde-acetal formed of general formula (I) is isolated. This can occur for example through adsorption on a strongly acid ion exchanger, e.g. a sulfonated styrene-divinyl benzene resin.

Since the compounds of general formula (I) in general are readily soluble in water, however, on occasion it is more advantageous to employ in the hydrolysis as base an alkaline earth metal hydroxide or oxide, e.g. calcium hydroxide, barium hydroxide or calcium oxide, and to undertake the neutralization of the reaction mixture with a neutralization agent, especially carbon dioxide, which forms a metal carbonate which is practically insoluble in water. Then by simple filtration of the precipitated salt there is obtained a practically pure aqueous solution of the glutamic acid-γ-semialdehyde-acetal, which can be employed directly for the production of proline. However, naturally it can also be concentrated to such an extent, in a given case under reduced pressure, that the glutamic acid-γ-semialdehyde-acetal is deposited in crystalline form.

In order to convert the glutamic acid-γ-semialdehyde-acetal of general formula (I) into D,L-proline, it is reacted at a pH between 0 and 4, preferably between 0.5 and 3 under the conditions of a catalytic hydrogenation. The required pH can be adjusted by an inorganic acid such as hydrochloric acid, sulfuric acid or phosphoric acid, or by an organic acid, such as oxalic acid, formic acid, acetic acid, benzene sulfonic acid or p-toluenesulfonic acid.

As solvent for the hydrogenation treatment there can be used water or a mixture of water and an organic solvent miscible therewith, such as methanol, ethanol, isopropyl alcohol, n-butanol, tetrahydrofurane or dioxane.

As hydrogenation catalyst there are generally preferred the metals of the 8th side group of the periodic system or suitable compounds thereof. The metals can be used as such or in known manner applied on suitable carriers. Especially preferred catalysts are palladium and platinum and/or their compounds. Examples of suitable catalysts are finely divided palladium metal, especially as palladium black, palladium bromide, palladium chloride, palladium iodide, palladium cyanide, palladium arsenide, palladium nitrate, palladium oxide or palladium sulfide or complex salts such as tetrachloropalladates, hexachloropalladates, tetraamine or diamine palladium chlorides as well as finely divided platinum metal, above all platinum black, or platinum oxide. Likewise there can be used platinum salts similar to the palladium salts.

If catalyst carriers are employed, preferred carriers for example are activated carbon, barium sulfate, silica gel, aluminum oxide or zeolites.

The hydrogenation catalysts are used suitably in an amount between 0.01 and 50 weight percent, preferably between 0.1 and 10 weight percent, calculated as active metal and based on the weight of the glutamic acid-γ-semialdehyde-acetal employed. The hydrogenation treatment is undertaken continuously or discontinuously in customary manner at a temperature between 0° and 200° C., preferably between 20° and 100° C., without excess pressure or at a hydrogen pressure of up to about 100 bar.

After the hydrogenation treatment the catalyst is separated from the reaction mixture and the D,L-proline formed is isolated in known manner, e.g. by means of an ion exchanger.

The invention is explained further in the following examples. Unless otherwise indicated all percentages are by weight.

The process can comprise, consist essentially of or consist of the stated steps with the recited materials.

EXAMPLE 1

16.3 Grams of 2-(2'-formylethyl)-1,3-dioxolane were dropped into a suspension of 48 grams of ammonium carbonate, 5.1 grams of hydrocyanic acid and 110 ml of aqueous ammonia (25%) at 35° C. in the course of one hour, and the mixture was further stirred for five hours at 40° C. Subsequently the salts were boiled out by increasing the temperature (up to 100° C. head temperature). The remaining aqueous solution was treated with 18.5 grams of calcium hydroxide and heated for 2.5 hours at 150° C. After cooling to 80° C. the reaction mixture was neutralized with solid carbon dioxide and the precipitated calcium carbonate filtered off. The aqueous filtrate was concentrated under vacuum and the remaining residue recrystallized from water-ethanol (volume ration 1:9). There were obtained 19.1 grams (87% of theory) of glutamic acid-γ-semialdehyde-ethylene-acetal (decomposition point ≧230° C.).

Elemental analysis: $C_7H_{13}NO_4$: Calculated: C, 47.99%; H, 7.48%; N, 7.80%. Found: C, 48.21%; H, 7.55%; N, 7.74%.

$^1$H-NMR-Spectrum ($D_2O$)

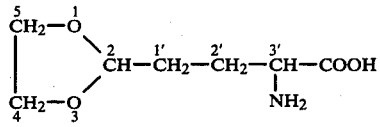

$\delta = 1.5–2.2$ (m, 4H): H-1', H-2'
$\delta = 3.75$ (t, 1H): H-3'
$\delta = 3.7–4.2$ (m, 4H): H-4, H-5
$\delta = 4.95$ (t, 1H): H-2

EXAMPLE 2

16.3 Grams of 2-(2'-formylethyl)-1,3-dioxolane were dropped into a suspension of 48 grams of ammonium carbonate, 5.1 grams of hydrocyanic acid and 110 ml of aqueous ammonia (25%) at 40° C. in the course of one hour, and the mixture was stirred for a further five hours at this temperature. Subsequently the salts were boiled off by increasing the temperature (up to 100° C. head temperature). The remaining aqueous solution was treated with 42 grams of barium hydroxide and heated for 1 hour at 160° C. After cooling to 60° C. the reaction mixture was neutralized with ammonium carbonate and the precipitated barium carbonate was filtered off. The filtrate was concentrated under vacuum and the residue recrystallized from water-dioxane. There were obtained 19.7 grams (90% of theory) of glutamic acid-γ-semialdehyde-ethylene-acetal.

EXAMPLE 3

A solution of 20.7 grams of 2-(2'-formylethyl)-1,3-dioxane in 50 ml of methanol was dropped into a suspension of 42 grams of ammonium carbonate, 6 grams of hydrocyanic acid and 120 ml of aqueous ammonia (25%) at 50° C. in the course of one hour, and the mixture was stirred for a further three hours at 50° C. Subsequently the methanol was distilled off up to a head temperature of 100° C. and the salts were boiled off. The remaining aqueous solution was treated with 21 grams of calcium hydroxide and heated for 2.5 hours at 150° C. After cooling to 80° C. it was neutralized with solid carbon dioxide and the precipiated calcium carbonate filtered off. The aqueous filtrate was concentrated under vacuum and the remaining residue recrystallized from water-ethanol (volume ratio 1:9). There were obtained 23.3 grams (86% of theory) of glutamic acid-γ-semialdehydepropylene-1,3-acetal.

Elemental analysis: $C_8H_{15}NO_4$: Calculated: C, 50.78%; H, 7.99%; N, 7.40%. Found: C, 51.31%; H, 8.15%; N, 7.35%.

EXAMPLE 4

17.2 Grams of 2-(2'-formylethyl)-5,5-dimethyl-1,3-dioxane dissolved in 50 ml of methanol was dropped into a suspension of 20 grams ammonium carbonate, 4.8 ml of hydrocyanic acid and 110 ml of aqueous ammonia (25%) at 40° C. in the course of one half hour after which the temperature was held for another 5 hours at 40° C. Subsequently the methanol was distilled off and through further heating to 100° C. the ammonium salts were boiled off. The remaining aqueous suspension was treated with 15 grams of calcium hydroxide and heated at 160° C. for 2 hours. After cooling to 80° C. the reaction mixture was neutralized with solid carbon dioxide and filtered. The filtrate was concentrated under vacuum and the residue recrystallized from water-ethanol (volume ratio 1:9). There was obtained 18.7 grams (86% of theory) of glutamic-acid-γ-semialdehyde-2,2-dimethylpropylene-1,3-acetal.

Elemental analysis: $C_{10}H_{19}NO_4$: Calculated: C, 55.28%; H, 8.81%; N, 6.45%. Found: C, 55.40%; H, 8.92%; N, 6.40%.

$^1$H-NMR-Spectrum ($D_2O$)

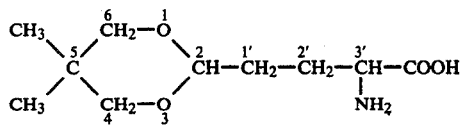

δ=0.75 (s,3H): 5-$CH_3$
δ=1.15 (s,3H): 5-$CH_3$
δ=1.5–2.2 (m,4H): H-1', H-2'
δ=3.65 (q, 4H): H-4, H-6
δ=3.75 (t,1H): H-3'
δ=4.65 (t,1H): H-2

EXAMPLE 5

2.0 Grams of glutamic acid-γ-semialdehydeethyleneacetal were dissolved in 15 ml of 0.5 N hydrochloric acid at room temperature, 1.0 gram of Pd/C (10% Pd) added and hydrogenated with hydrogen at 1 bar up to the calculated take up amount (250 ml). After separating the catalyst and concentrating the filtrate there was obtained 80.9% of theory of thin layer chromatographically pure D,L-proline in the form of its hydrochloride.

EXAMPLE 6

6.0 Grams of glutamic acid-γ-semialdehydeethyleneacetal were dissolved in 50 ml of 0.25 N hydrochloric acid at room temperature, 2.5 grams of Pd/C (10% Pd) added and hydrogenation carried out at 25° C. in an autoclave at 20 bar $H_2$ pressure up until complete conversion.

After working up there was obtained 85.2% of theory of thin layer chromatographically pure D,L-proline in the form of its hydrochloride.

EXAMPLE 7

10.0 Grams of glutamic acid-γ-semialdehydeethylene-acetal were hydrogenated according to Example 6 at 50° C. After working up there was obtained 83.7% of thin layer chromatographically pure D,L-proline in the form of its hydrochloride.

EXAMPLE 8

5.0 Grams of glutamic acid-γ-semialdehydeethyleneacetal were hydrogenated in 50 ml of 0.1 N sulfuric acid according to Example 5. There was obtained 84.2% of thin layer chromatographically pure D,L-proline as its sulfate.

EXAMPLE 9

6.0 Grams of glutamic acid-γ-semialdehydeethyleneacetal were hydrogenated in 50 ml of 90% aqueous formic acid according to Example 6. The working up yielded 83.0% of free D,L-proline.

EXAMPLE 10

4.0 Grams of glutamic acid-γ-semialdehydeethyleneacetal were hydrogenated according to Example 5. The hydrochloric acid solution was concentrated, the residue taken up in 15 ml of water and passed over a weakly basic ion exchange resin. The proline containing eluate was concentrated up to dryness. There were obtained 2.23 grams of D,L-proline free from other aminoacids (84.8% of theory) with melting point 208°–213° C. (decomposition).

EXAMPLE 11

2.0 Grams of glutamic acid-γ-semialdehydeethyleneacetal were hydrogenated with 0.3 grams of platinum oxide according to Example 6. There was obtained after working up 81% of thin layer chromatographically pure D,L-proline in the form of its hydrochloride.

EXAMPLE 12

2.0 Grams of glutamic acid-γ-semialdehyde-2,2-dimethylpropylene-1,3-acetal were treated with 1.0 gram of Pd/C (10% Pd) and 15 ml of 0.1 N hydrochloric acid and hydrogenated in an autoclave at 50 bar and 50° C. until complete conversion. The working up gave 81.5% of thin layer chromatographically pure D,L-proline in the form of its hydrochloride.

EXAMPLE 13

18.9 Grams of glutamic acid-γ-semialdehydepropylene-1,3-acetal were dissolved in 150 ml of 0.1 N hydrochloric acid, 5 grams of Pd/C (5% Pd) added and hydrogenation carried out with hydrogen at room temperature under normal pressure until complete reaction occurred. After working up there were obtained 13.0 grams (86.0%) of D,L-proline hydrochloride, in thin layer chromatographically pure form. From this after dehydrohalogenation with a weakly basic ion exchanger there were obtained 9.78 grams (85.0%) of D,L-proline. Melting point: 207°–212° C. (decomposition).

The entire disclosure of German priority application No. P 30 43 159.5-42 is hereby incorporated by reference.

What is claimed is:

1. A cyclic acetal of glutamic acid-γ-semialdehyde of the formula

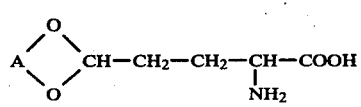

in which A is an alkylene group with 2 to 3 carbon atoms or such an alkylene group substituted by 1 to 2 methyl groups.

* * * * *